United States Patent [19]

Okushima et al.

[11] 4,265,816
[45] May 5, 1981

[54] PROCESS FOR PREPARING STEROID-CARBOXYLATES

[75] Inventors: Hiromi Okushima, Kawasaki; Shinichiro Fujimori, Machida; Rikizo Furuya; Shuzo Hayakawa, both of Yokohama, all of Japan

[73] Assignee: Mitsubishi Chemical Industries, Ltd., Tokyo, Japan

[21] Appl. No.: 145,693

[22] Filed: May 1, 1980

[30] Foreign Application Priority Data

May 14, 1979 [JP] Japan ................................ 54-58969

[51] Int. Cl.$^3$ .............................................. C07J 9/00
[52] U.S. Cl. ...................... 260/239.55 C; 260/239.57; 260/397.1
[58] Field of Search ........ 260/397.1, 239.57, 239.55 C

[56] References Cited

U.S. PATENT DOCUMENTS

| 3,734,938 | 5/1973 | Hodosan et al. | 260/397.1 |
| 3,738,983 | 6/1973 | Dryden et al. | 260/239.57 |

Primary Examiner—Elbert L. Roberts
Attorney, Agent, or Firm—Oblon, Fisher, Spivak, McClelland & Maier

[57] ABSTRACT

An alkali metal salt of a 3-(17β-hydroxyandrosten-3-one 3-acetal-17α-yl)propiolic acid which is useful as an intermediate in the preparation of 3-(3-oxo-7α-acetylthio-17β-hydroxyandrost-4-en-17α-yl)-propiolactone (spironolactone) as antialdosteronic diuretics and hypotensive agents is prepared by reacting a 17β-hydroxypregnen-20-yn-3-one 3-acetal (I) with an alkali metal dimsyl (II) to give an alkali metal salt of the 17β-hydroxypregnen-20-yn-3-one 3-acetal (III), and reacting the compound (III) with carbon dioxide followed by hydrolysis.

1 Claim, No Drawings

PROCESS FOR PREPARING STEROID-CARBOXYLATES

BACKGROUND OF THE INVENTION

1. Field of the Invention

This invention relates to a process for preparing a steroidcarboxylate. More particularly, it relates to a process for preparing an alkali metal salt of a 3-(17β-hydroxyandrosten-3-one 3-acetal-17α-yl)propiolic acid (hereinafter referred to as HAP).

2. Description of the Prior Art

The alkali metal salt of HAP prepared by the process of the invention is useful as an intermediate in the preparation of 3-(3-oxo-7α-acetylthio-17β-hydroxyandrost-4-en-17α-yl)-propiolactone (hereinafter referred to as "spironolactone") which is in turn useful as anti-aldosteronic diuretics and hypotensive agents and which are prepared from the alkali metal salt of HAP according to the following equation:

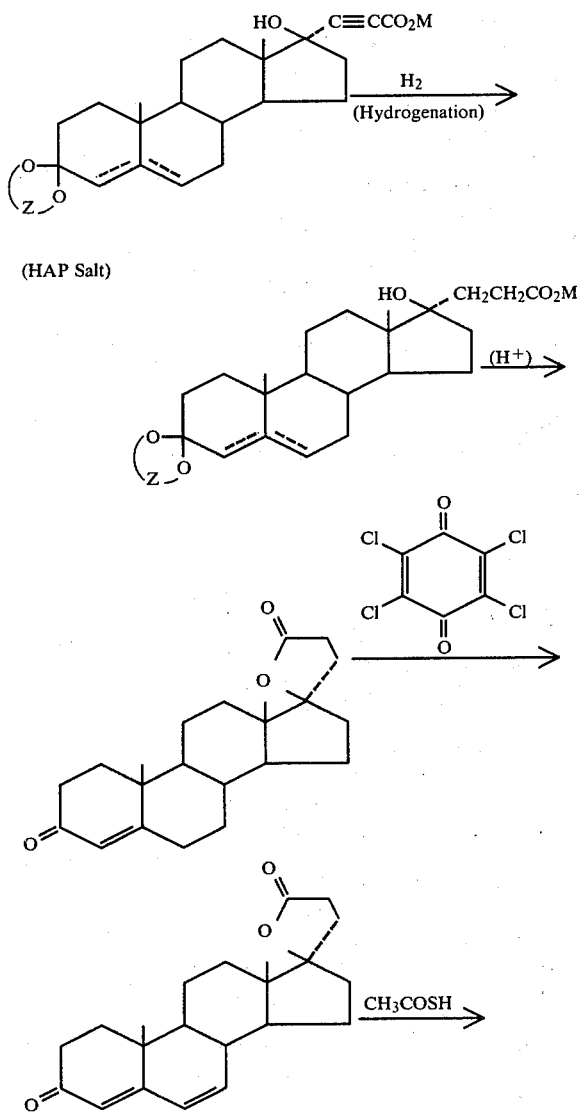

(HAP Salt)

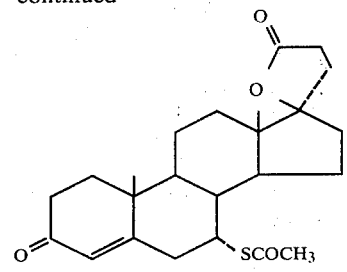

(Spironolactone)

For the preparation of the spironolactone a process has been known which starts from 3β-hydroxyandrost-5-en-17-one. According to the process, 3β-hydroxyandrost-5-en-17-one is ethynylated and then reacted with carbon dioxide to give a propiolic acid derivative, which is then hydrogenated into an acrylic acid derivative.

The acrylic acid derivative is then converted by acid treatment into 3-(3β,17β-dihydroxyandrost-5-en-17α-yl)acrylolacetone, which is hydrogenated into a saturated lactone, which is subsequently subjected to the Oppenauer oxidation to give a 3-(17β-hydroxyandrost-4-en-3-on-17α-yl)propiolactone [see, J. A. Cella, E. A. Brown and R. R. Burtner, J. Org. Chem., 24, 743 (1959)].

The resulting 3-(17β-hydroxyandrost-4-en-3-on-17α-yl)propiolactone is thereafter dehydrogenated at the 6,7-positions and then reacted with thioacetic acid to give the spironolactone [see, J. A. Cella and R. C. Tweit, J. Org. Chem., 24, 1109 (1959)].

One of the disadvantages of the above-mentioned process is the use of 3β-hydroxyandrost-5-en-17-one as a starting material which involves some problems as described hereinafter. Another disadvantage of the process is that it is complicated due to the great number of steps involved therein.

3β-Hydroxyandrost-5-en-17-one used in the prior art process is prepared, via a complicated process comprising 6 steps, from diosgenin which is extracted from the roots of Dioscorea, one of Bardasco, naturally growing in mountainous regions in Mexico. For this reason in combination with the difficult culture of Bardasco, 3β-hydroxyandrost-5-en-17-one becomes increasingly very expensive.

On the other hand, a process capable of preparing inexpensively androst-4-ene-3,17-dione has been developed in recent years, which process resorts to microbiological oxidation of steroids such as cholesterol derived from fish oil or wool grease recoverable from waste washings of wool.

Thus, it is an object of the invention to provide a simpler process for preparing an alkali metal salt of HAP that is an important intermediate for the spironolactone, starting from the inexpensive androst-4-en-3,17-dione instead of the costly 3β-hydroxyandrost-5-en-17-one.

It has already been known that the HAP alkali metal salts can be prepared from androst-4-ene-3,17-dione. For example, Japanese Patent Laid-Open (Kokai) No. 28157/1978 describes that lithium 3-(17β-hydroxyandrost-4-en-3-one 3-acetal-17α-yl)propiolate is obtained by reacting 17β-hydroxypregn-4-en-20-yn-3-one 3-acetal with an organolithium compound and reacting the resulting lithium salt of 17β-hydroxypregn-4-en-20-yn-3-on 3-acetal with carbon dioxide. While this process has an advantage in that metallization can be directly performed, the alkyl lithium used in the metallization is difficult to handle and expensive. Accordingly there is a need for improvement in the process.

SUMMARY OF THE INVENTION

Thus, in accordance with the invention, there is provided a process for preparing a steroid-carboxylate comprising reacting a 17β-hydroxypregnen-20-yn-3-one 3-acetal of the formula:

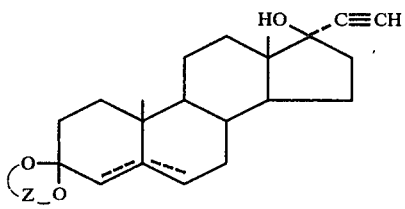

wherein Z is an alkylene group having not more than 10 carbon atoms and the dotted lines in rings A and B represent a double bond at the 4- or 5-position, with an alkali metal dimsyl of the formula:

$[CH_3SOCH_2]^{\ominus} \cdot M^{\oplus}$ (II)

wherein M is an alkali metal atom, to give an alkali metal salt of the 17β-hydroxypregnen-20-yn-3-one 3-acetal having the formula:

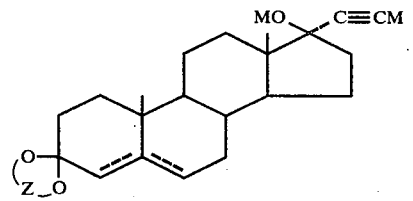

wherein Z, M and the dotted lines in rings A and B are as defined in the above formulas (I) and (II), and reacting the compound of formula (III) with carbon dioxide followed by hydrolysis to give an alkali metal salt of a 3-(17β-hydroxyandrosten-3-one 3-acetal-17α-yl)-propiolic acid having the formula:

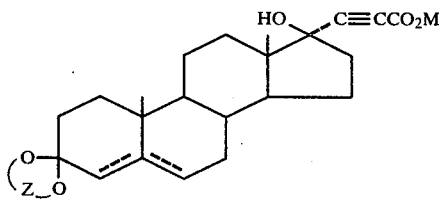

wherein Z, M and the dotted lines in rings A and B are as defined in the above formulas (I) and (II).

DETAILED DESCRIPTION OF THE PREFERRED EMBODIMENTS

Now the present invention is described in detail.

The starting material used in the process according to the invention is a 17β-hydroxypregnen-20-yn-3-one 3-acetal of the above formula (I), in which Z is an alkyl-ene group having not more than 10 carbon atoms, preferably an alkylene group having 2 or 3 carbon atoms. Examples of the 17β-hydroxypregnen-20-yn-3-one 3-acetal include 17β-hydroxypregn-4-en-20-yn-3-one 3-ethylene acetal, 17β-hydroxypregn-4-en-20-yn-3-one 3-propylene acetal, 17β-hydroxypregn-5-en-20-yn-3-one 3-ethylene acetal and the like.

In the above formula (II) which represents alkali metal dimsyls, M is an alkali metal atom such as lithium, sodium and potassium. Examples of the alkali metal dimsyl are lithium dimsyl, sodium dimsyl, potassium dimsyl, etc.

The alkali metal dimsyl may be prepared in a conventional manner by reaction of dimethyl sulfoxide and an alkali metal hydride or reaction of dimethyl sulfoxide and an alkali metal in dispersion. This reaction may be carried out in an organic solvent such as, for example, dimethyl sulfoxide, tetrahydrofuran, diglyme or dioxane.

The alkali metal dimsyl is used usually in an amount of 2 to 20 moles, preferably 3 to 6 moles per mole of 17β-hydroxypregnen-20-yn-3-one 3-acetal. If the amount of alkali metal dimsyl is too small, the 17β-hydroxypregnen-20-yn-3-one 3-acetal is insufficiently metallized so that the subsequent carbonation step does not proceed sufficiently. Conversely, an excessively large amount of alkali metal dimsyl is disadvantageous economically and brings about an increased exotherm in the carbonation step. Accordingly neither an excessively small nor large amount of alkali metal dimsyl is preferred.

The reaction temperature is usually in the range of $-20°$ to $65°$ C. and preferably from $20°$ to $50°$ C. Neither a higher nor lower temperature is preferred, since at a lower temperature the metallization of the 17β-hydroxypregnen-20-yn-3-one does not proceed sufficiently, whereas a higher reaction temperature may result in a decreased yield and degradation of the alkali metal dimsyl.

The reaction time is usually in the range of 2 to 4 hours.

The amount of dimethyl sulfoxide at the beginning of the metallization reaction must be kept usually to a level of about 6 moles or less per mole of alkali metal dimsyl and preferably as small as possible, since the presence of an excessively large amount of dimethyl sulfoxide leads to a decreased yield in the metallization of the 17β-hydroxypregnen-20-yn-3-one.

The reaction of 17β-hydroxypregnen-20-yn-3-one 3-acetal and alkali metal dimsyl is usually carried out in an inert solvent such as tetrahydrofuran, diglyme or dioxane.

Thus, an alkali metal salt of the 17β-hydroxypregnen-20-yn-3-one 3-acetal represented by the above formula (III) is obtained by the reaction of a 17β-hydroxypregnen-20-yn-3-one 3-acetal and an alkali metal dimsyl. Usually the reaction product is used directly in the subsequent carbonation step without isolation.

The reaction of an alkali metal salt of 17β-hydroxypregnen-20-yn-3-one 3-acetal with carbon dioxide may be carried out by a method known per se (see, for example, Japanese Patent Laid-Open (Kokai) No. 28157/1978) wherein a solution or suspension of the alkali metal salt of 17β-hydroxyprenen-20-yn-3-one 3-acetal in an inert solvent as exemplified above is brought into contact with gaseous carbon dioxide.

The reaction temperature is usually in the range of −70° to 50° C., preferably −30° to 20° C. The reaction pressure varies depending on reaction temperature and a superatmospheric pressure may be used if desired.

The reaction of an alkali metal salt of 17β-hydroxy-pregnen-20-yn-3-one 3-acetal and carbon dioxide gives an alkali metal salt of 3-(17β-alkali metal-oxy-androsten-3-one 3-acetal-17α-yl)propiolic acid represented by the formula:

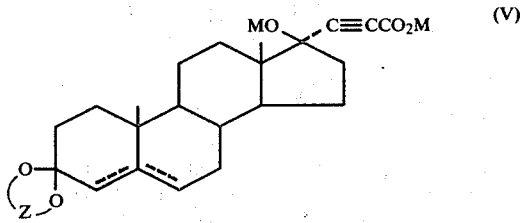

wherein Z, M and the dotted lines in rings A and B are as defined in the above formulas I and II.

Hydrolysis of the resulting alkali metal salt of 3-(17β-alkali metal-oxy-androsten-3-one 3-acetal-17α-yl)propiolic acid may be also carried out by a method known per se (see, for example, Japanese Patent Laid-Open (Kokai) No. 28157/1978). For example, water can be added to the reaction mixture of the alkali metal salt of 17β-hydeoxypregnen-20-yn-3-one 3-acetal and carbon dioxide to hydrolyze the reaction product selectively at the 17β-position.

After completion of the hydrolysis, the solvent may be distilled off to isolate the desired alkali metal salt of 3-(17β-hydroxyandrosten-3-one 3-acetal-17α-yl)propiolic acid as crystals. Alternatively the organic layer may be separated from the aqueous layer without distillation of solvent to give the desired alkali metal salt of 3-(17β-hydroxyandrosten-3-one 3-acetal-17α-yl)propiolic acid in solution.

As stated above, the alkali metal salt of 3-(17β-hydroxyandrosten-3-one 3-acetal-17α-yl)propiolic acid thus obtained may be subjected successively to hydrogenation, acid treatment, oxidation with chloranil and addition of thioacetic acid in a convention manner in order to prepare the finally desired spironolactone.

Hydrogenation of the alkali metal 3-(17β-hydroxyandrosten-3-one 3-acetal-17α-yl)propiolate is carried out catalytically in an inert solvent as described above in the presence of a catalyst. The catalysts useful for the hydrogenation include Raney nickel, a noble metal such as palladium on activated charcoal, a nickel boride catalyst obtained by reacting a nickel salt with a borohydride, and the like.

In accordance with the process of the present invention, an intermediate for use in the preparation of the spironolactone can be readily prepared from an inexpensive steroid with high yield under mild conditions.

Having generally described this invention, a more complete understanding can be obtained by reference to certain examples which are provided herein for purposes of illustration only and are not intended to be limiting in any manner.

PREPARATION (Preparation of sodium dimsyl)

To a liquid mixture of 40 ml of dimethyl sulfoxide and 250 ml of tetrahydrofuran 10.4 g of sodium hydride was added at 70° C. under nitrogen atmosphere and stirred for 4 hours. Thus a reagent in a slurry form was prepared.

EXAMPLE

To 500 ml of tetrahydrofuran was added 26.0 g of a mixture of 17β-hydroxypregn-4-en-20-yn-3-one 3-ethylene acetal (3,3-ethylenedioxy-17β-hydroxypregn-4-en-20-yn) and 17β-hydroxypregn-5-en-20-yn-3-one 3-ethylene acetal (3,3-ethylenedioxy-17β-hydroxypregn-5-en-20-yn), and the resulting mixture was added at room temperature to the slurry reagent as prepared in the above preparation and stirred for 2 hours.

The reaction mixture was then cooled to −20° C. and gaseous carbon dioxide was passed through the mixture with stirring for 2 hours. The reaction mixture was then allowed to warm to room temperature, whereupon 450 ml of water was added and the resulting mixture was then stirred for 30 minutes.

Subsequently tetrahydrofuran was completely distilled off and the residue was cooled to 10° C. and filtered. The filter cake was washed and dried to give 32.4 g of a mixture of sodium 3,3-ethylenedioxy-17β-hydroxy-17α-pregn-5-en-20-yn-21-carboxylate and sodium 3,3-ethylenedioxy-17β-hydroxy-17α-pregn-4-en-20-yn-21-carboxylate (90.5% purity) as a solid.

The solid product was dissolved in 1,890 ml of methanol and a hydrogenation catalyst was added to the solution. The mixture was then subjected to hydrogenation at 55° C. under a hydrogen pressure of 10 kg/cm² for about 4 hours. The hydrogenation catalyst used was prepared by adding dropwise a solution of 2.3 g of sodium borohydride in 125 ml of water to 2.69 g of nickel chloride hexahydrate supported on 6.74 g of activated charcoal.

After the hydrogenation was complete, the catalyst was filtered out of the reaction solution. To the filtrate 25 ml of aqueous 35% hydrochloric acid was added and the mixture was heated at 50° C. for an hour for deacetalization, whereupon the reaction mixture was neutralized with aqueous 7% sodium hydrogen carbonate solution and methanol was then distilled off. The residue was worked up by extraction with benzene and evaporation of benzene to dryness to give 26.3 g of 3-(17β-hydroxyandrost-4-en-3-one-17α-yl)propiolactone, the purity of which was 86.1%.

Having now fully described the invention, it will be apparent to one of ordinary skill in the art that many changes and modifications can be made thereto without departing from the spirit of the invention as set forth herein.

What is claimed as new and intended to be covered by Letters Patent is:

1. A process for preparing a steroid-carboxylate comprising reacting a 17α-hydroxypregnen-20-yn-3-one 3-acetal of the formula:

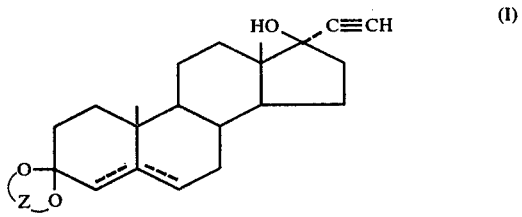

wherein Z is an alkylene group having not more than 10 carbon atoms and the dotted lines in rings A and B represent a double bond at the 4- or 5-position, with an alkali metal dimsyl of the formula:

$$[CH_3SOCH_2]^{\ominus} \cdot M^{\oplus} \qquad (II)$$

wherein M is an alkali metal atom, to give an alkali metal salt of the 17β-hydroxypregnen-20-yn-3-one 3-acetal having the formula:

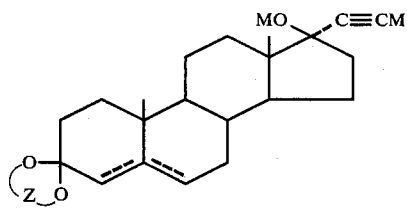
(III)

wherein Z, M and the dotted lines in rings A and B are as defined in the above formulas (I) and (II), and reacting the compound of formula (III) with carbon dioxide followed by hydrolysis to give an alkali metal salt of a 3-(17β-hydroxyandrosten-3-one 3-acetal-17α-yl)propiolic acid having the formula:

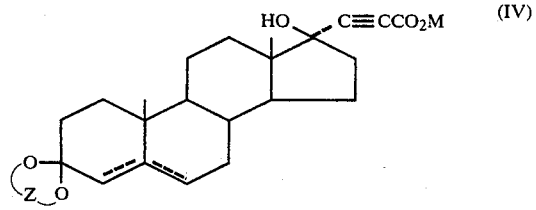
(IV)

wherein Z, M and the dotted lines in rings A and B are as defined in the above formulas (I) and (II).

* * * * *